(12) United States Patent
Paasch et al.

(10) Patent No.: US 7,011,634 B2
(45) Date of Patent: Mar. 14, 2006

(54) URINE SAMPLE COLLECTION DEVICE

(75) Inventors: Robert W. Paasch, Aumsville, OR (US); Michael J. Woodward, Aumsville, OR (US)

(73) Assignee: Sample Rite, Inc., Aumsville, OR (US)

( * ) Notice: Subject to any disclaimer, the term of this patent is extended or adjusted under 35 U.S.C. 154(b) by 0 days.

(21) Appl. No.: 10/825,615

(22) Filed: Apr. 14, 2004

(65) Prior Publication Data
US 2004/0267158 A1    Dec. 30, 2004

Related U.S. Application Data

(60) Provisional application No. 60/462,986, filed on Apr. 14, 2003.

(51) Int. Cl.
*A61B 5/00* (2006.01)
*A61M 1/00* (2006.01)

(52) U.S. Cl. .................. 600/573; 600/574; 604/317; 4/144.1

(58) Field of Classification Search ............... 600/573, 600/574, 575, 584; 604/317, 318, 322–327; 4/144.1–144.4, 301, 305, 661; 422/61, 102; 220/738, 694
See application file for complete search history.

(56) References Cited

U.S. PATENT DOCUMENTS

| | | | | |
|---|---|---|---|---|
| 4,137,573 A | * | 2/1979 | Kroeger ..................... 4/144.1 |
| 4,203,169 A | * | 5/1980 | Dale ....................... 73/863.52 |
| 5,060,317 A | * | 10/1991 | Bertelsen .................... 4/144.2 |
| 5,146,637 A | * | 9/1992 | Bressler et al. ................ 4/445 |
| 6,151,972 A | * | 11/2000 | Venter et al. ............. 73/863.41 |
| 6,212,698 B1 | * | 4/2001 | Stingley et al. ................ 4/315 |
| 6,434,762 B1 | * | 8/2002 | Gordon ........................ 4/483 |
| D489,453 S | * | 5/2004 | Sapyta ..................... D24/128 |
| 6,811,754 B1 | * | 11/2004 | House ....................... 422/102 |

* cited by examiner

*Primary Examiner*—Charles Marmor
(74) *Attorney, Agent, or Firm*—Marger Johnson & McCollom, P.C.

(57) ABSTRACT

A urine collection device includes a support apparatus for supporting the urine collection device on a toilet. An attachment section attaches to a sample holder and a collection section receives and directs urine into the sample holder.

22 Claims, 3 Drawing Sheets

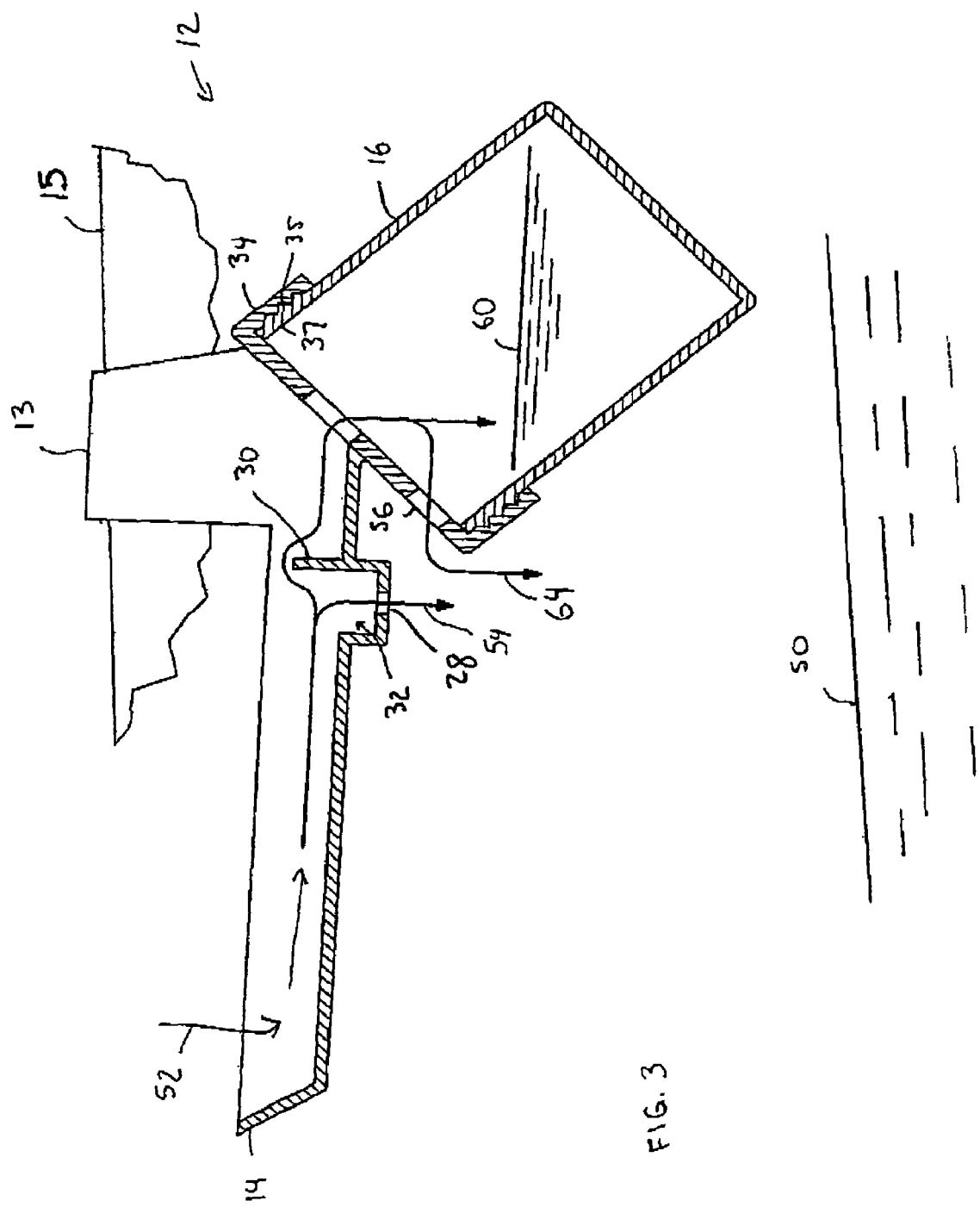

URINE SAMPLE COLLECTION DEVICE

This application claims the benefit of Provisional Application No. 60/462,986, filed Apr. 14, 2003.

BACKGROUND

It is difficult for many people to hold a urine sample cup effectively to catch their own urine stream flow. It is even more difficult for the elderly, disabled, overweight, pregnant and very young to give urine samples. It is not easy or sanitary for anyone. Trying to catch a "mid-stream" flow multiplies the difficulties. A mid-stream flow refers to a urine sample that does not include the initial portion of a urine stream. In other words, a urine sample taken after the patent has already started urinating. Mid-stream urine samples can be important, since the initial portion of the urine stream may be contaminated.

When patients or sample-givers are faced with the indignity of someone else holding the urine sample cup for them, it sometimes becomes impossible for the patient to pass urine on demand. It is also time consuming, unsanitary and difficult for the nurses.

A "nurse's hat" is a large plastic disposable pot that looks like an upside down hat in which the brim is the funnel and the bowl collects the urine flow. After the urine sample is deposited into the nurse's hat, the nurse pours a portion of the urine into a sample cup. This is time consuming and unsanitary for the nurses and patients. The nurse's hat also becomes a medical waste disposal issue because it is large and bulky and creates a large volume of waste.

The present invention addresses this and other problems associated with the prior art.

SUMMARY OF THE INVENTION

A support apparatus supports a urine collection device on a toilet. An attachment section attaches to a sample holder and a collection section receives and directs urine into the sample holder. The urine collection device allows most people to collect their own urine sample easily and effectively. The sample device has the advantage of collecting a "mid-stream" urine flow thus eliminating having to pour a urine sample into a sample cup. The device is easy to use, economical to manufacture, and allows people to give a urine sample in privacy.

The foregoing and other objects, features and advantages of the invention will become more readily apparent from the following detailed description of a preferred embodiment of the invention which proceeds with reference to the accompanying drawings.

BRIEF DESCRIPTION OF THE DRAWINGS

FIG. 3 is a side-sectional view of the USCD.

DETAILED DESCRIPTION

Figure 1:
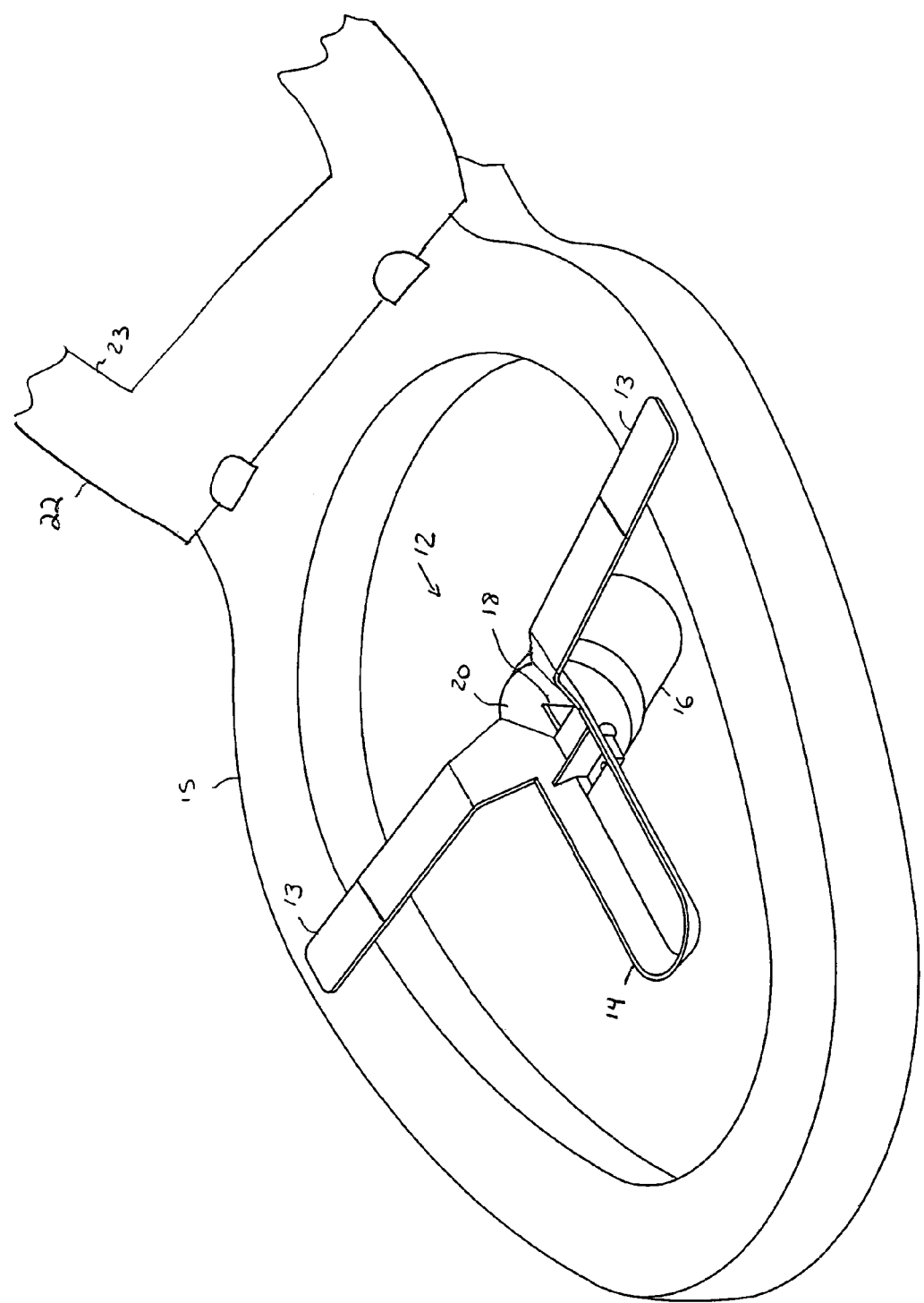
FIG. 1 is a perspective view of the Urine Sample Collection Device (USCD) installed on a toilet.

Referring to FIG. 1, the Urine Sample Collection Device (USCD) 12 is a hands-free, self-supporting urine sample funneling and mid-stream collecting system for male and female people. The USCD 12 includes support arms 13 that support the USCD 12 on top of a toilet bowl 15. A collection section 14 collects urine from a user and funnels the urine toward an opening 18 in a sample cup attachment section 20. A urine sample cup 16 is attached underneath section 20 for retaining the urine funneled down from collection section 14.

The USCD 12 collects the urine sample by first being placed on the toilet bowl 15 or on top of the toilet seat 22. The thinness and narrow width of the support arms 13 allow the USCD 12 to be placed on top of the toilet bowl 15 and the toilet seat 22 placed down on top of the USCD 12 and bowl 15. The USCD 12 is secured in position by the weight of the user sitting on top of the toilet seat 22. In an alternative embodiment, the USCD 12 is placed across the ring 23 of the toilet seat 22.

The USCD 12 is placed generally in the middle of the toilet bowl 15 or toilet seat 22 with the collection section 14 being directed forward toward a front end of the toilet bowl 15. The collection section 14 thereby is positioned directly under the urinary track of the user. This allows a person providing a urine sample to sit down on the toilet seat 22 and pass urine in a normal manner.

Figure 2:
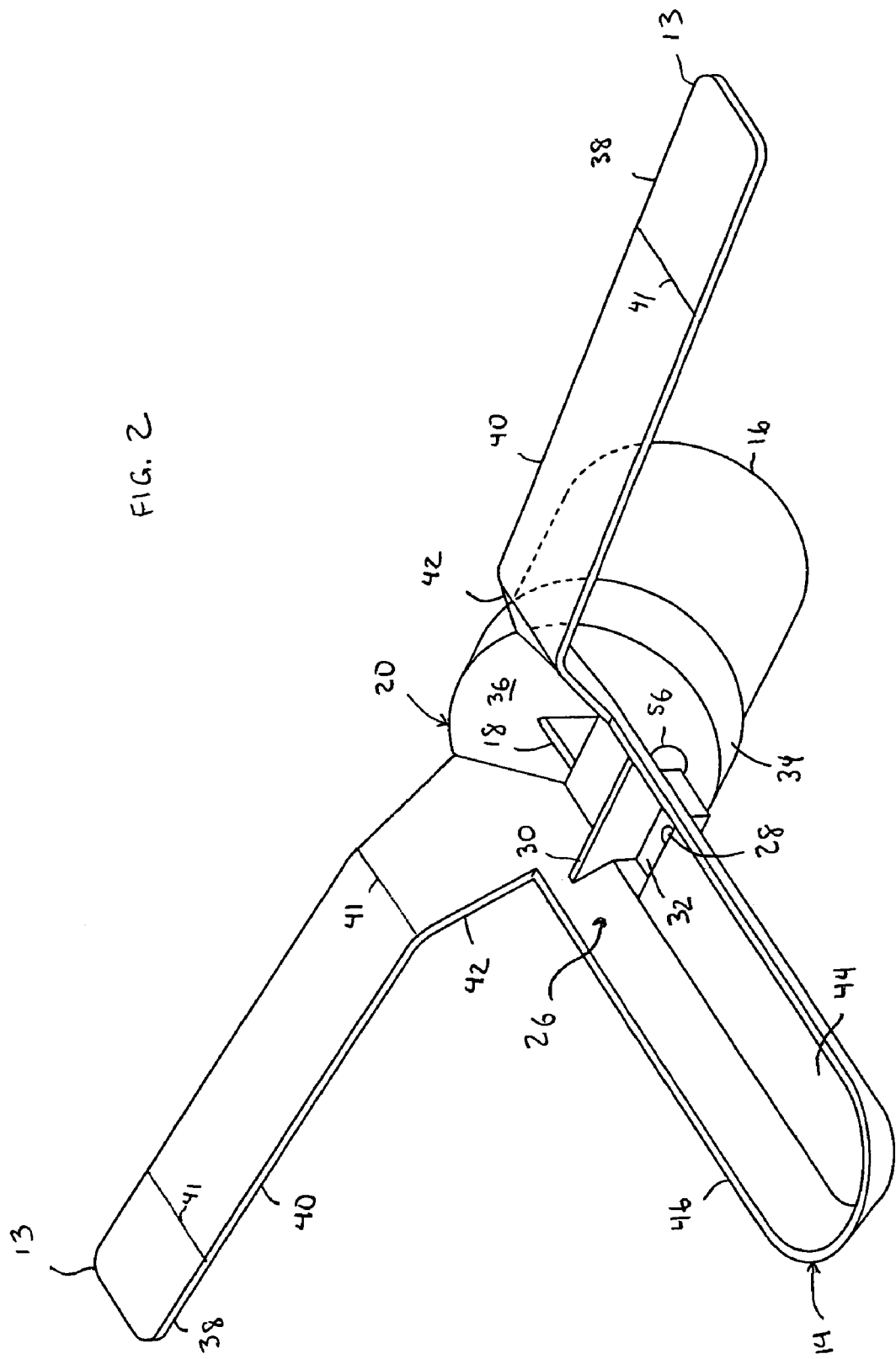
FIG. 2 is perspective isolation view of the USCD.

FIG. 2 shows the USCD 12 in an isolation view. The support arms 13 include opposite flat sections 38 that sit on top of the toilet bowl of toilet seat (see FIG. 1). Intermediate sections 40 can be bent slightly at an angle of about 15 degrees from horizontal lowering the collection section 14 and attachment section 20 below the top of the toilet bowl. Opposite support arm center sections 42 are angled approximately 45 degrees from horizontal and attach to the attachment section 20.

In one embodiment, the support arms 13 extend approximately 13 inches from the attachment section 20 to the ends and are approximately 1.5 inches wide. The length of the support arms 13 are sized to sit on top of any conventional toilet, however, the length can be varied for other toilet bowl widths. The support arms 13 can be made out of any material with enough strength to span the toilet and hold the USCD 12 and any urine samples. For example, a cardboard or plastic material can be used. The support arms 13 can include perforations 41 that are used to break the support arms 13 apart after use. This allows the USCD 12 to be more easily disassembled for inserting into a garbage can.

The angles of support arm sections 40 and 42 are set so the sample cup 16 sits at an angle above the conventional water level in the toilet bowl. However, for toilets that may have a higher water level, the angles of support arm sections 40 and 42 can be manually manipulated to sit higher in the toilet bowl. Alternatively, the support arms 13 can be made during manufacture with different angles for different toilet bowl water levels.

The collection section 14 includes a flat bottom section 44 and an upwardly and outwardly rising sidewall 46. The collection section 14 in one embodiment slopes upwardly from the attachment section 20 at an angle of approximately 15 degrees above horizontal. This further promotes the urine to flow downward toward opening 18. The collection section 14 in one example is approximately 4.5 inches long and 1.5–2 inches wide.

The collection section 14 is located directly under and in front of the urinary excretion point of the user. If for any reason the collection section 14 is not sitting in the proper location to catch the urine of the user, the support arms 13 can be repositioned on the toilet bowl and the arms bent to accommodate different anatomical characteristics of the urine sample provider.

The collection section 14 includes a flow divider 26 that allows collection of the urine "mid-stream" flow by redirecting a first portion of the urine flow out a bottom hole 28 and into the toilet bowl. The hole 28 is located in a chamber 32 that is approximately 2 cubic centimeters (ccs) in volume. As a user first starts to urinate, a first portion of the urine flows from the collection section 14 into chamber 32. The initial urine flow passes slowly out of chamber 32 through hole 28 and into the toilet.

The rate that the urine drains from hole 28 is much slower than the typical rate that urine flows into the chamber 32 from a user. Therefore, as the user continues to urinate, urine fills up and overflows chamber 32 and flows further downward toward opening 18 in the attachment section 20. The urine flowing into opening 18 is then collected in sample cup 16. This mid-stream flow sample is therefore cleaner and a more representative sample of the urine in the bladder compared with the first portion of the urine flow captured in chamber 32 and discharged out of hole 28.

A dam 30 can optionally be used to further prevent the initial urine flow from reaching the sample cup 16. The dam 30 extends upwardly from the back of the chamber 32 and in front of the opening 18. The dam 30 does not extend upwards as high as wall 46 of the collection section 14 so urine will not overflow over the wall 46. However, the dam 30 is high enough to further restrict the initial urine flow from flowing over the chamber 32 and into opening 18. If the purity of the urine is not of utmost importance, then another embodiment of the invention can be provided that does not provide the flow divider 26 or the dam 30 in collector section 14.

The attachment section 20 includes a rearwardly sloping back wall 36. The back wall 36 in combination with the angles of the middle sections 42 create a larger collection area that funnels the received urine into the opening 18. The attachment section 20 also includes a cap section 34 that receives the sample cup 16. Another unique feature is the ability of the sample cup 16 to be easily attached and detached to the cap section 34. The cap section 34 also includes an overflow hole 56 used for urine that overflows sample cup 16. The overflow hole 56 will be described in further detail below.

FIG. 3 is a side-sectional view of the USCD 12. A urine flow 52 is received by the collection section 14. The collection section 14 directs the initial urine flow into the chamber 32. An initial urine flow 54 flows into chamber 32 and through hole 28 into the bowl 15. As the chamber 32 fills up, the additional midflow urine rises above the dam 30 and flows through hole 18 and into sample cup 16.

The overflow hole 56 is located on the bottom side of the cap section 34 directly underneath the collection section 14. In cases when there is large amounts of urination, the urine 60 in sample cup 16 increases to the top of the left edge of the sample cup 16. Additional excess urine overflows through the overflow hole 56, over the left edge corner of the cap section 34, and into the water 50 in toilet bowl 15. Since the sample cup 16 is positioned at an angle, urine 64 will overflow through overflow opening 56 before the sample cup 16 is completely full. Thus, when the sample cup 16 is moved to an upright position, the urine 60 will only fill a portion of the sample cup 16.

As mentioned above, in one example, the sample cup 16 is held at an approximately 45 degree angle by the cap section 34 when sitting in the operational position inside the toilet bowl. However, the angle of the sample cup 16 can be larger or smaller angle according to what proportion of the sample cup 16 is desired to be filled with urine before excess urine overflows into the toilet.

The cap section 34 includes threads 35 on an inside wall that are used for threadedly engaging with a top end 37 of the sample cup 16. Thus, the sample cup 16 in this embodiment is screwed into the cap section 34. However, in alternative embodiments, the cap section 34 can be sized so that the sample cup 16 is slide or snapped into place in cap section 34. In the snapped embodiment, clips (not shown) may be located in the attachment section 34 for clipping onto the top end of the sample cup 16. In the force fit embodiment, the attachment section 34 may be slightly oval in shape to press in the sides of the sample cup 16. After the urine sample is given, the sample cup 16 is disconnected from USCD 12 and saved. In the embodiment shown in FIG. 3, the sample cup 16 is screwed out of the cap section 34. In other force fit of snap in embodiments, the sample cup is slid out of the cap section 34.

The USCD 12 can be made out of any of several types of plastic, elastomer, composite, coated paper, wire frame, or metal. In one example, the USCD 12 is made out of a coated paper or thin semi-rigid plastic material that is discarded after one use. Alternatively, the USCD 12 can be made out of a material that can be sanitized for reuse with other sample cups. In this type of embodiment, the USCD 12 may be made out of metal, heavy plastic or other non-porous rigid materials that can withstand the temperatures and high water forces used with heavy sanitization.

The USCD 12 can be used wherever urine samples are taken such as: medical clinics; doctor's office; hospitals; nursing homes and drug testing businesses, etc. The USCD can be one integral piece or several pieces attached together. The different sections may also be made from different materials. For example, the support arms 13 may be detachable from the attachment section 20 and the collection section 14. This would allow different pieces to be reused.

The USCD 12 has several unique benefits. It facilitates the collection of a urine sample by being hands-free. It has the capability to catch a "mid-stream" flow. The mid-stream flow is sometimes important, since the initial urine excretion may be contaminated by other substances. The USCD 12 can be a disposable one-time-use product and has a removable sample cup 16 attached directly to the rest of the USCD 12. The compact size and design also reduces the quantity of medical waste and is easily stackable for shipping multiple components at the same time.

Having described and illustrated the principles of the invention in a preferred embodiment thereof, it should be apparent that the invention may be modified in arrangement and detail without departing from such principles. We claim all modifications and variation coming within the spirit and scope of the following claims.

The invention claimed is:

1. A urine collection device, comprising:
 a support apparatus for supporting the urine collection device on a toilet;
 an attachment section for attaching to a sample holder;
 a collection section for receiving and directing urine into the sample holder; and
 a flow divider located in the collection section that separates a first portion of the urine away from the sample holder;
 wherein the flow divider includes a cavity in the collection section that collects the first portion of the urine and a hole at a bottom end of the cavity that directs the first portion of the urine into the toilet.

2. The urine collection device according to claim 1 including a dam located between the cavity and the attachment section for further directing the first portion of the urine into the cavity.

3. A urine collection device, comprising:
a support apparatus for supporting the urine collection device on a toilet;
an attachment section for detachably coupling to a sample holder; and
a collection section including an elongated channel integrally formed with the support apparatus for receiving and directing urine into the sample holder;
wherein the support apparatus includes oppositely opposed arms extending in opposite directions from the attachment section.

4. The urine collection device according to claim 3 including a flow divider located in the collection section that separates a first portion of the urine away from the sample holder.

5. The urine collection device according to claim 4 wherein the flow divider includes a cavity in the collection section that collects the first portion of the urine and a hole at a bottom end of the cavity that directs the first portion of the urine into the toilet.

6. The urine collection device according to claim 5 including a dam located between the cavity and the attachment section for further directing the first portion of the urine into the cavity.

7. The urine collection device according to claim 3 wherein the elongated channel extends from a front face of the attachment section at an upwardly directed angle toward a top front surface of the toilet.

8. The urine collection device according to claim 3 wherein the attachment section includes an opening in a front face that directs urine from the collection section into the sample holder.

9. The urine collection device according to claim 3 wherein the attachment section includes a cap section that is detachably coupled to the sample holder and that substantially covers an open end of the sample holder.

10. The urine collection device according to claim 9 wherein the cap section is threaded to screwingly engage a sample holder cup.

11. A urine collector, comprising:
a support apparatus for supporting the urine collector on a toilet;
a collection section for receiving the urine; and
a cap section for detachably coupling to and substantially covering a removable sample cup and directing the urine from the collection section into the sample cup;
wherein the cap section includes a first opening for receiving the urine from the collection section and a second overflow opening that allows urine to overflow from the sample cup into the toilet.

12. The urine collector according to claim 11 including a preflow divider for directing a first portion of the received urine away from the sample cup and into the toilet.

13. The urine collector according to claim 12 wherein the preflow divider includes a chamber in the collection section temporarily retaining the first portion of the urine and a hole in the chamber directing the first portion of the urine into the toilet.

14. The urine collector according to claim 11 wherein the collection section extends slightly below a top end of the toilet and angles downward from a front end of the toilet towards a middle section of the toilet.

15. The urine collector according to claim 11 wherein the support apparatus sits on a top end of a toilet bowl and a toilet seat sits down on top of the support apparatus.

16. A urine collector, comprising:
a support apparatus for supporting the urine collector on a toilet;
a collection section for receiving the urine;
a cap section for coupling to a removable sample cup and directing the urine from the collection section into the sample cup; and
a preflow divider for directing a first portion of the received urine away from the sample cup and into the toilet;
wherein the preflow divider includes a chamber in the collection section temporarily retaining the first portion of the urine and a hole in the chamber directing the first portion of the urine into the toilet.

17. A urine collector, comprising:
a support apparatus far supporting the urine collector on a toilet;
a collection section for receiving the urine;
a cap section for coupling to a removable sample cup and directing the urine from the collection section into the sample cup; and
a preflow divider for directing a first portion of the received urine away from the sample cup and into the toilet;
wherein the cap section includes a first opening for receiving the urine from the collection section and a second overflow opening that allows urine to overflow from the sample cap into the toilet.

18. The urine collector according to claim 17 wherein the cap section holds the sample cup at an angle that causes the urine to overflow out of the second overflow opening when the sample cup is only partially full of urine.

19. A urine sample collection device, comprising:
an apparatus configured to sit on a toilet bowl and receive urine, the apparatus including an elongated channel funneling the received urine into a detachable sample cup and a dam that prevents an initial portion of the urine from entering the sample cup.

20. The urine sample collection device according to claim 19 including a flow divider that separates an initial portion of the urine from entering the sample cup.

21. The urine sample collection device according to claim 19 including an overflow opening that causes a portion of the urine in the sample cup to overflow into the toilet before the urine completely fills up the sample cup.

22. The urine sample collection device according to claim 19 including support arms that sit on opposite sides of the toilet for holding the sample cup in the toilet bowl above a toilet bowl water level.

* * * * *

UNITED STATES PATENT AND TRADEMARK OFFICE
CERTIFICATE OF CORRECTION

| | | |
|---|---|---|
| PATENT NO. | : 7,011,634 B2 | Page 1 of 1 |
| APPLICATION NO. | : 10/825615 | |
| DATED | : March 14, 2006 | |
| INVENTOR(S) | : Paasch et al. | |

It is certified that error appears in the above-identified patent and that said Letters Patent is hereby corrected as shown below:

On the Title Page, under References Cited, item 56 please replace "6,434,762 B1" with --6,434,762 B2--

On the Title Page, under References Cited, item 56 please replace "6,811,754 B1" with --6,811,754 B2--

Column 6, line 35, please replace "sample cap" with --sample cup--

Signed and Sealed this

Sixth Day of March, 2007

JON W. DUDAS
*Director of the United States Patent and Trademark Office*